United States Patent
Brule et al.

(10) Patent No.: US 10,252,960 B2
(45) Date of Patent: Apr. 9, 2019

(54) METHOD FOR TRANSFORMING SUGARS AND SUGAR ALCOHOLS INTO MONO- AND POLY-OXIDIZED COMPOUNDS IN THE PRESENCE OF A HETEROGENEOUS CATALYST

(71) Applicant: IFP Energies nouvelles, Rueil-Malmaison (FR)

(72) Inventors: Emilie Brule, Lyons (FR); Etienne Girard, Lyons (FR); Amandine Cabiac, Givors (FR); Damien Delcroix, St. Maurice l'Exil (FR); Marc Jacquin, Lyons (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 0 days.

(21) Appl. No.: 15/739,921

(22) PCT Filed: Apr. 21, 2016

(86) PCT No.: PCT/EP2016/058820
§ 371 (c)(1),
(2) Date: Dec. 26, 2017

(87) PCT Pub. No.: WO2016/206826
PCT Pub. Date: Dec. 29, 2016

(65) Prior Publication Data
US 2018/0179131 A1 Jun. 28, 2018

(30) Foreign Application Priority Data
Jun. 26, 2015 (FR) ..................... 15 55966

(51) Int. Cl.
| | |
|---|---|
| *C07C 27/00* | (2006.01) |
| *C07C 29/132* | (2006.01) |
| *C07C 29/60* | (2006.01) |
| *C07C 29/00* | (2006.01) |
| *B01J 21/06* | (2006.01) |
| *B01J 23/34* | (2006.01) |
| *C01G 23/00* | (2006.01) |
| *C01G 25/02* | (2006.01) |
| *C01G 45/12* | (2006.01) |
| *C07C 31/18* | (2006.01) |
| *C07H 3/02* | (2006.01) |
| *C07H 3/06* | (2006.01) |
| *C07B 41/06* | (2006.01) |
| *C07B 41/08* | (2006.01) |
| *C07B 41/12* | (2006.01) |

(52) U.S. Cl.
CPC ............ *C07C 27/00* (2013.01); *B01J 21/063* (2013.01); *B01J 21/066* (2013.01); *B01J 23/34* (2013.01); *C01G 23/006* (2013.01); *C01G 25/02* (2013.01); *C01G 45/125* (2013.01); *C07C 29/00* (2013.01); *C07C 29/132* (2013.01); *C07C 29/60* (2013.01); *C07C 31/18* (2013.01); *C07H 3/02* (2013.01); *C07H 3/06* (2013.01); *C01P 2002/34* (2013.01); *C07B 41/06* (2013.01); *C07B 41/08* (2013.01); *C07B 41/12* (2013.01)

(58) Field of Classification Search
CPC ......... C07C 31/18; C07C 27/00; C07C 27/04; C07C 29/00; C07C 29/60; C07C 29/132; B01J 21/063; B01J 21/066; B01J 23/34; C10G 23/006; C10G 25/02; C10G 45/125; C07H 3/02; C07H 3/06; C10P 2002/34; C01P 2002/34
See application file for complete search history.

(56) References Cited

U.S. PATENT DOCUMENTS

| | | | |
|---|---|---|---|
| 4,366,332 A | 12/1982 | Chao | |
| 4,496,780 A * | 1/1985 | Arena | B01J 23/78 502/327 |
| 4,880,758 A * | 11/1989 | Heistand, II | C01B 13/185 423/594.1 |
| 2016/0090331 A1* | 3/2016 | Girard | B01J 23/002 536/124 |

FOREIGN PATENT DOCUMENTS

WO 2015055315 A1 4/2015

OTHER PUBLICATIONS

International Search Report PCT/EP2016/058820 dated Jun. 17, 2016.

* cited by examiner

*Primary Examiner* — Yate' K Cutliff
(74) *Attorney, Agent, or Firm* — Millen, White, Zelano and Branigan, P.C.

(57) ABSTRACT

The invention concerns a method for converting a feedstock selected from sugars or sugar alcohols, alone or in a mixture, into mono- or polyoxygenated compounds, wherein the feedstock is contacted with at least one heterogeneous catalyst comprising a support selected from perovskites of formula $ABO_3$, in which A is selected from the elements Mg, Ca, Sr and Ba and B is selected from the elements Fe, Mn, Ti and Zr, and the oxides of elements selected from lanthanum, neodymium, yttrium and cerium, alone or in a mixture, which oxides can be doped with at least one element selected from alkali metals, alkaline earths and rare earths, in a reducing atmosphere, at a temperature of 100° C. to 300° C. and at a pressure of 0.1 MPa to 50 MPa.

16 Claims, No Drawings

METHOD FOR TRANSFORMING SUGARS AND SUGAR ALCOHOLS INTO MONO- AND POLY-OXIDIZED COMPOUNDS IN THE PRESENCE OF A HETEROGENEOUS CATALYST

FIELD OF THE INVENTION

The invention relates to the conversion of bio-sourced compounds into intermediate products of chemistry and the use of hydrothermally stable basic substrates without adding an additional base for the transformation of sugars and sugar alcohols into mono- or poly-oxidized compounds.

PRIOR ART

The transformation of sugars and sugar alcohols into mono- or poly-oxidized compounds is conventionally carried out in a basic medium by combining a base that consists of an oxide or a salt of alkaline or alkaline-earth metal with a heterogeneous catalyst that consists of a hydrogenating metal deposited on a substrate in the presence of hydrogen pressure.

For example, the patent application WO 2015/055315 of Biochemtex claims the combination of NaOH with Ru, which is deposited on carbon, alumina or zirconia, for transforming sorbitol and xylitol, by themselves or in a mixture, at 200° C. under 60 bar (25° C.) of hydrogen into ethylene glycol, propylene glycol, and glycerol.

The U.S. Pat. No. 4,366,332 of Hydrocarbon Research claims the combination of $Ca(OH)_2$ with Ni with a silica or alumina substrate for transforming sorbitol at 240° C. under 120 bar (25° C.) of hydrogen into ethylene glycol, propylene glycol, and glycerol.

The drawback of the use of a base in combination with the heterogeneous catalyst is the formation of organic salts that should be neutralized and separated from the reaction medium. Works were carried out in the prior art to work without an additional base.

For example, in Catalysis Communications, 2013, 39, 86-89, Mu et al. describe the transformation of sorbitol at 200° C. under 40 bar of hydrogen (25° C.) into glycols and glycerol in the presence of a single heterogeneous catalyst that consists of Ni deposited on an Ni/MgO magnesium oxide with a ratio of 3/7 between Ni and Mg. The hydrothermal stability of this substrate is poor and brings about a loss of activity and selectivity. More than 10% of gaseous non-oxidized products are in addition obtained with a partial conversion of sorbitol of approximately 70%.

The U.S. Pat. No. 4,496,780 of UOP claims the transformation of polyols including glucose, fructose, and sorbitol by hydrocracking lighter polyols including glycerol, ethylene glycol and propylene glycol in the presence of a single heterogeneous catalyst that comprises a noble metal of group VIII of the periodic table deposited on a solid substrate doped by an alkaline-earth metal oxide. For example, the transformation of sorbitol in water at 180° C. under 220 bar of hydrogen in the presence of a catalyst that comprises ruthenium deposited on an alumina titanate doped with barium oxide ($Ru/TiO_2$—$Al_2O_3$—$BaO$) makes it possible to obtain ethylene glycol, propylene glycol, and glycerol. Under hydrothermal conditions, the ruthenium on alumina particles aggregate, which brings about a loss in activity and selectivity and makes a regeneration of the catalyst necessary.

These catalytic systems therefore make it possible to transform sugar alcohols into poly-oxidized products without adding an additional base but they are not hydrothermally stable. There is therefore a need for hydrothermally stable basic substrates for the transformation of sugars and sugar alcohols into mono- and poly-oxidized compounds without adding an additional base.

Under hydrothermal conditions, the large specific surface area of the substrates used for depositing the hydrogenating metal brings about the modification of textural properties of the substrate that can bring about the aggregation of supported metal particles and therefore the deactivation of the catalyst, requiring regular regeneration steps. There is therefore a need for hydrothermally stable substrates for the transformation of sugars and sugar alcohols into mono- and poly-oxidized compounds.

This invention therefore proposes the use of new heterogeneous catalysts that consist of a hydrogenating metal that is deposited on a hydrothermally stable basic substrate, and this without adding an additional base.

For several years, there has been a sharp interest in the incorporation of products of renewable origin within the fuel and chemistry networks, in addition to or as a substitute for products of fossil origin. The lignocellulosic biomass is an abundant source of renewable carbon. The cellulose and hemicellulose constituting the lignocellulosic biomass can easily be depolymerized into glucose and xylose. These sugars can be catalytically hydrogenated into their equivalent sugar alcohols, sorbitol and xylitol for example. The hydrogenolysis of these sugars and sugar alcohols under basic conditions provides access to industrially very important poly-oxidized chemical intermediate products such as ethylene glycol, propylene glycol and glycerol. Under the same hydrogenolysis conditions, mono-oxidized chemical intermediate products, which are just as important, such as methanol, ethanol or propanol, can also be obtained.

The hydrogenolysis of sugars and sugar alcohols into mono- or poly-oxidized compounds is conventionally carried out in an aqueous, basic medium by combining a base that consists of an oxide or a salt of alkaline or alkaline-earth metal with a heterogeneous catalyst that consists of a hydrogenating metal that is deposited on a substrate in the presence of hydrogen pressure and at temperatures of higher than 100° C. In the prior art, there is not described a catalytic system that makes possible a transformation of sugars or sugar alcohols without adding an additional base and using a heterogeneous catalyst that consists of a hydrothermally stable basic support on which the hydrogenating metal is deposited. We therefore propose to transform a feedstock that is selected from among sugars and sugar alcohols, by themselves or in a mixture, by bringing said feedstock into contact with at least one heterogeneous catalyst that comprises a hydrothermally stable basic substrate that is selected from among the perovskites of $ABO_3$ structure and the oxides of elements that are selected from among lanthanum, neodymium, yttrium, cerium, by themselves or in a mixture, with said oxides being doped by an alkaline metal and/or an alkaline-earth and/or an element that is selected from among the rare earths, of the type of those described in this invention, without adding an additional base.

The works of the applicant made it possible to demonstrate that bringing a feedstock that is selected from among sugars and sugar alcohols, by themselves or in a mixture, without adding an additional base, into contact with at least one hydrothermally stable heterogeneous catalyst, as claimed, in a reaction chamber that operates under specific operating conditions, made it possible to obtain mono- or poly-oxidized products as claimed.

OBJECT OF THE INVENTION

An object of this invention is therefore to provide a method for transforming a feedstock that is selected from among sugars and sugar alcohols, by themselves or in a mixture, into mono- or poly-oxidized compounds, in which said feedstock is brought into contact with at least one heterogeneous catalyst in the presence of at least one solvent, with said solvent being water, an alcohol, a diol, or another solvent, under a reducing atmosphere, and at a temperature of between 100° C. and 300° C., and at a pressure of between 0.1 MPa and 50 MPa, without adding an additional base, in which said heterogeneous catalyst(s) comprise(s) at least one metal that is selected from among the metals of groups 8 to 11 of the periodic table and a substrate that is selected from among the perovskites of formula $ABO_3$, in which A is selected from among the elements Mg, Ca, Sr and Ba, and B is selected from among the elements Fe, Mn, Ti and Zr, and the oxides of elements that are selected from among lanthanum, neodymium, yttrium, cerium, by themselves or in a mixture, with said oxides able to be doped by at least one element that is selected from among the alkaline metals, the alkaline-earths, and the rare earths, by themselves or in a mixture, with said method being performed without adding additional catalyst.

In this invention, reference is made to the new notation of the periodic table: Handbook of Chemistry and Physics, 76$^{th}$ Edition, 1995-1996.

Heterogeneous catalyst is defined as a catalyst that is not soluble under the operating conditions of the reaction.

One advantage of this invention is to make it possible to obtain upgradeable mono- or poly-oxidized products from sugars or sugar alcohols, by themselves or in a mixture, in the presence of a hydrothermally stable heterogeneous catalyst and without adding an additional base.

Hydrothermal stability is defined as a preservation of the structure of the substrate and the heterogeneous catalyst, observable by X-ray diffraction, and a preservation of the texture of the substrate and the heterogeneous catalyst, observable by adsorption-desorption of nitrogen, for example. Preferably, the specific surface area of the substrate and the heterogeneous catalyst is preserved. The specific surface area of the substrate and of the heterogeneous catalyst after reaction is preferably reduced by a maximum of 30% in relation to that of the substrate and the heterogeneous catalyst before reaction and in a very preferred manner reduced by a maximum of 20% in relation to that of the substrate and of the heterogeneous catalyst before reaction.

DETAILED DESCRIPTION OF THE INVENTION

The Feedstock

The feedstock that is treated in the method according to the invention is a feedstock that is selected from among sugars and sugar alcohols, by themselves or in a mixture.

Sugar is defined as any oligosaccharide or monosaccharide that is soluble under the reaction conditions called for by the invention.

Monosaccharides refer more particularly to the carbohydrates of the general formula $C_x(H_2O)_x$ or $C_xH_{2x}O_x$, with x an integer of between 3 and 6 inclusive. The preferred monosaccharides that are used as a feedstock in this invention are selected from among dihydroxyacetone (x=3), erythrose (x=4), xylose (x=5), arabinose (x=5), glucose (x=6), mannose (x=6), and fructose (x=6), taken by themselves or in a mixture.

Preferably, the sugar feedstock that is used in the method according to the invention is selected from among cellobiose, dihydroxyacetone, erythrose, xylose, fructose, and glucose, taken by themselves or in a mixture.

In a very preferred manner, said feedstock is selected from among xylose, fructose, and glucose, taken by themselves or in a mixture.

Oligosaccharide more particularly refers to a carbohydrate that has as an empirical formula $C_{6n}H_{10n+2}O_{5n+1}$ or $C_{5n}H_{8n+2}O_{4n+1}$, where n is an integer that is greater than 1, with the monosaccharide units comprising said oligosaccharide being identical or not, and a carbohydrate having as an empirical formula $(C_{6m}H_{10m+2}O_{5m+1})(C_{5n}H_{8n+2}O_{4n+1})$, where m and n are integers that are greater than or equal to 1, with the monosaccharide units composing said oligosaccharide being identical or not. The oligosaccharides are preferably selected from among the oligomers of pentoses and/or hexoses with a degree of polymerization that makes it possible for them to be soluble under reaction conditions called for by the invention. They can be obtained by partial hydrolysis of polysaccharides obtained from renewable resources such as starch, inulin, cellulose, or hemicellulose, optionally obtained from lignocellulosic biomass. For example, vapor explosion of the lignocellulosic biomass is a method for partial hydrolysis of cellulose and hemicellulose contained in the lignocellulosic biomass that produces a stream of oligosaccharides and monosaccharides. The preferred oligosaccharides that are used as a feedstock in this invention are selected from among saccharose, lactose, maltose, isomaltose, inulobiose, melibiose, gentiobiose, trehalose, cellobiose, cellotriose, cellotetraose, and the oligosaccharides that are obtained from the hydrolysis of said polysaccharides that are obtained from the hydrolysis of starch, inulin, cellulose or hemicellulose, taken by themselves or in a mixture.

Sugar alcohol more particularly refers to the molecules that are obtained by hydrogenation of the oligosaccharide and monosaccharide sugars defined above.

In the case where sugar alcohols are obtained by hydrogenation of oligosaccharide sugars, said sugar alcohols advantageously respond either to the general formula $C_{6n}H_{10n+4}O_{5n+1}$ or $C_{5n}H_{8n+4}O_{4n+i}$, where n is an integer that is greater than 1, or to the following general formula $(C_{6m}H_{10m+2}O_{5m+1})(C_{5n}H_{8n+2}O_{4n+1})H_2$, where m and n are integers that are greater than or equal to 1. The preferred sugar alcohols that are used as a feedstock in this invention obtained by hydrogenation of the oligosaccharide sugars are selected from among lactitol, maltitol, isomaltitol, inulobitol, melibitol, gentiobitol, cellobitol, cellotritol and cellotetritol, taken by themselves or in a mixture.

The sugar alcohols that are obtained by hydrogenation of monosaccharide sugars advantageously have the following general formula $C_x(H_2O)_xH_2$ or $C_xH_{2x+2}O_x$, with x an integer of between 3 and 6 inclusive. The preferred sugar alcohols that are used as a feedstock in this invention obtained by hydrogenation of monosaccharide sugars are selected from among glycerol (x=3), erythritol (x=4), xylitol (x=5), arabinitol (x=5), sorbitol (x=6), and mannitol (x=6), taken by themselves or in a mixture.

Thus, the sugar alcohol feedstock that is used in the method according to the invention is selected from among lactitol, maltitol, isomaltitol, inulobitol, melibitol, gentiobitol, cellobitol, cellotritol, cellotetritol, glycerol, erythritol, xylitol, arabinitol, sorbitol, mannitol, taken by themselves or in a mixture.

Preferably, the sugar alcohol feedstock that is used in the method according to the invention is selected from among cellobitol, glycerol, erythritol, xylitol, sorbitol, mannitol, taken by themselves or in a mixture.

In a very preferred manner, said feedstock is selected from among xylitol, sorbitol, and mannitol, taken by themselves or in a mixture.

The Catalysts

In accordance with the invention, said feedstock is brought into contact, in the method according to the invention, with only at least one heterogeneous catalyst as defined below in the presence of at least one solvent, with said solvent being water, an alcohol, a diol, or another solvent, under a reducing atmosphere, and at a temperature of between 100° C. and 300° C., and at a pressure of between 0.1 MPa and 50 MPa.

In accordance with the invention, said heterogeneous catalyst(s) comprise(s) at least one metal that is selected from among the metals of groups 8 to 11 of the periodic table and a substrate that is selected from among the perovskites of formula $ABO_3$, in which A is selected from among the elements Mg, Ca, Sr and Ba, and B is selected from among the elements Fe, Mn, Ti and Zr, and the oxides of the elements selected from among lanthanum (La), neodymium (Nd), yttrium (Y), cerium (Ce), by themselves or in a mixture, with said oxides able to be doped by at least one element that is selected from among the alkaline metals, the alkaline-earths, and the rare earths, by themselves or in a mixture.

In the case where several heterogeneous catalysts as defined above are used in the method according to the invention, said catalysts can be identical or different.

In a preferred embodiment, a single heterogeneous catalyst as defined above is used in the method according to the invention.

Said metals that are selected from among the metals of groups 8 to 11 of the periodic table of the heterogeneous catalyst(s) according to the invention are preferably selected from among the following metals: Fe, Ru, Os, Co, Rh, Ir, Ni, Pd, Pt, Cu, Ag, Au, taken by themselves or in a mixture.

In a preferred manner, said metal is selected from among the metals Ru, Rh, Ir, Ni, Pd, Pt, Cu, taken by themselves or in a mixture.

In a very preferred manner, said metal is selected from among the metals Ru, Ni, Pt, taken by themselves or in a mixture.

In the case where the metal of said heterogeneous catalyst(s) is selected from among the following noble metals: Ru, Os, Rh, Pd, Pt, Ag, Au, the noble metal content in said heterogeneous catalyst(s) is advantageously between 0.1% and 10% by weight and in a preferred manner between 0.1% and 5% by weight in relation to the total mass of said heterogeneous catalyst(s).

In the case where the metal of said heterogeneous catalyst(s) is selected from among non-noble metals, the non-noble metal content in said heterogeneous catalyst(s) is advantageously between 0.1% and 40% by weight and in a preferred manner between 0.1% and 30% by weight in relation to the total mass of said heterogeneous catalyst(s).

The metal(s) of the heterogeneous catalyst(s) according to the invention is/are advantageously deposited on a substrate.

In accordance with the invention, said heterogeneous catalyst(s) comprise(s) a substrate that is selected from among the perovskites of formula $ABO_3$, in which A is selected from among the elements Mg, Ca, Sr and Ba, and B is selected from among the elements Fe, Mn, Ti and Zr, and the oxides of the elements that are selected from among lanthanum (La), neodymium (Nd), yttrium (Y), cerium (Ce), by themselves or in a mixture, with said oxides able to be doped by at least one element that is selected from among the alkaline metals, the alkaline-earths, and the rare earths, by themselves or in a mixture.

Non-limiting examples of perovskite are: $BaTiO_3$, $SrTiO_3$, $BaZrO_3$, $CaZrO_3$, $SrZrO_3$, $CaMnO_3$.

In the case where said substrate is selected from among the doped oxides, the doping element is selected from among the alkaline metals, the alkaline-earths, and the rare earths, by themselves or in a mixture.

In the case where said substrate is selected from among the oxides that are doped by at least one element that is selected from among the alkaline metals, said doping element is advantageously selected from among the elements Li, Na, K, Rb, Cs and preferably from among Li, Na, K.

In the case where said substrate is selected from among the oxides that are doped by at least one element that is selected from among the alkaline-earths, said doping element is advantageously selected from among Be, Mg, Ca, Sr, Ba, and preferably from among Ca, Sr, Ba.

In the case where said substrate is selected from among the oxides that are doped by at least one element that is selected from among the rare earths, said doping element is advantageously selected from among La, Ce, Sm, Gd, Y, Pr.

Preferably, the content of doping element that is selected from among the alkaline metals, the alkaline-earths and the rare earths, by themselves or in a mixture, is advantageously between 0.1% and 30% by weight and in a preferred manner between 1 and 20% by weight in relation to the total mass of said substrate.

In a preferred manner, the substrate of said heterogeneous catalyst(s) is selected from among the perovskites.

In another preferred embodiment, the substrate of said heterogeneous catalyst(s) is the cerium oxide that can be doped.

The BET specific surface area of the substrate is advantageously less than 200 $m^2/g$, in a preferred manner less than 150 $m^2/g$, in a preferred manner less than 100 $m^2/g$, in a preferred manner less than 70 $m^2/g$, and in a more preferred manner less than 50 $m^2/g$.

Said substrate is hydrothermally stable according to the invention, i.e., stable under conditions that combine water and temperature.

Hydrothermal stability is defined as a preservation of the structure of the substrate, observable by X-ray diffraction, and a preservation of the texture of the substrate, observable by adsorption-desorption of nitrogen, for example. Preferably, the specific surface area of the substrate is also preserved. The specific surface area of the substrate after reaction is preferably reduced by a maximum of 30% in relation to that of the substrate before reaction and in a very preferred manner reduced by a maximum of 20% in relation to that of the substrate before reaction.

Thus, the substrate can advantageously undergo a treatment step prior to its use in the method according to the invention whose purpose is to improve its stability under the hydrothermal conditions of the reaction. It is possible to cite, for example, the surface passivation, the deposition of carbon film, the deposition of oxide.

The deposition of the metal(s) selected from among groups 8 to 11 of the periodic table on said substrate of the heterogeneous catalyst(s) according to the invention generally involves a precursor of the metal(s). For example, it can be a matter of metal organic complexes, metal salts such as metal chlorides, metal nitrates, metal carbonates.

The introduction of the metal(s) can advantageously be done by any technique that is known to one skilled in the art, such as, for example, ion exchange, dry impregnation, excess impregnation, vapor phase deposition, etc. The introduction of metal can be carried out before or after the shaping of the substrate.

The step for introducing the metal(s) can advantageously be followed by a heat treatment step. The heat treatment is advantageously carried out between 300° C. and 700° C., under an atmosphere of oxygen or air. The heat treatment step can be followed by a temperature reduction treatment. The reducing heat treatment is advantageously carried out at a temperature of between 200° C. and 600° C. under a stream of hydrogen or under a hydrogen atmosphere.

Preferably, said heterogeneous catalyst(s) also undergo an in-situ reduction step, i.e., in the reactor where the reaction takes place, before the introduction of the reaction feedstock. Said reduction step can also advantageously be carried out ex-situ.

The heterogeneous catalyst(s) used in this invention can be in the form of powder, extrudates, balls or pellets. The shaping can be done before or after the introduction of metal.

The BET specific surface area of the heterogeneous catalyst is advantageously less than 200 $m^2/g$, in a preferred manner less than 150 $m^2/g$, in a preferred manner less than 100 $m^2/g$, in a preferred manner less than 70 $m^2/g$, and in a more preferred manner less than 50 $m^2/g$.

According to the invention, said heterogeneous catalyst is hydrothermally stable, i.e., stable under conditions that combine water and temperature.

Hydrothermal stability is defined as a preservation of the structure of the heterogeneous catalyst, observable by X-ray diffraction, and a preservation of the texture of the heterogeneous catalyst, observable by adsorption-desorption of nitrogen, for example. Preferably, the specific surface area of the heterogeneous catalyst is also preserved. The specific surface area of the heterogeneous catalyst after reaction is preferably reduced by a maximum of 30% in relation to that of the heterogeneous catalyst before reaction and in a very preferred manner reduced by a maximum of 20% in relation to that of the heterogeneous catalyst before reaction.

Hydrothermal stability is also defined as preservation of the chemical composition of the heterogeneous catalyst, observable by elementary analysis. In a preferred manner, the elementary chemical composition of the heterogeneous catalyst is preserved. The chemical composition of each element of the heterogeneous catalyst after reaction is thus, in a preferred manner, reduced by a maximum of 30% in relation to that of the heterogeneous catalyst before reaction, in a very preferred manner reduced by a maximum of 20% in relation to that of the heterogeneous catalyst before reaction.

The heterogeneous catalyst(s) used in this invention are characterized by the techniques that are known to one skilled in the art. Transmission microscopy will be cited, for example, to characterize the metal phase, X-ray diffraction to characterize the structure of the heterogeneous catalyst, adsorption-desorption of nitrogen to characterize the texture of the heterogeneous catalyst, and X fluorescence to measure the chemical composition of the heterogeneous catalyst.

In accordance with the invention, said method is performed without adding additional catalyst. In particular, said method according to the invention is performed without adding additional basic catalyst. In a preferred manner, said method according to the invention is performed without adding basic catalyst that is selected from among the oxides, hydroxides and alcoholates of alkaline or alkaline-earth metals, which may or may not be hydrated, having as a general formula $M_mX_n.n'$ $H_2O$, in which the metal M is a metal that is selected from among the metals of groups 1 and 2 of the periodic table, m is a whole number of between 1 and 2, n is a whole number of between 1 and 2, and n' is a number of between 0 and 20, and X is selected from among oxygen, the hydroxyl group or the alcoholate groups of general formula OR with R an alkyl group.

Transformation Method

In accordance with the invention, the method for transformation of the feedstock that is selected from among sugars and sugar alcohols, by themselves or in a mixture, is implemented in a reaction chamber in the presence of at least one solvent, with said solvent being water, an alcohol, a diol, by themselves or in a mixture, under a reducing atmosphere, and at a temperature of between 100° C. and 300° C., and at a pressure of between 0.1 MPa and 50 MPa.

The method is therefore implemented in a reaction chamber that comprises at least one solvent and in which said feedstock is brought into the presence of the heterogeneous catalyst according to the invention.

In accordance with the invention, the method according to the invention is performed in the presence of at least one solvent, with said solvent being water, an alcohol, a diol, by itself or in a mixture.

The diols are advantageously selected from among ethylene glycol and propylene glycol.

The alcohols are advantageously selected from among methanol, ethanol and propanols.

In the case where said method according to the invention is performed in the presence of water, the mixture of solvents comprises a content by mass of water that is greater than 5% by weight and in a preferred manner greater than 30%, and in a very preferred manner greater than 50% in relation to the total mass of said mixture.

According to another embodiment, the method according to the invention is performed only in the presence of water.

In accordance with the invention, the method for transformation of said feedstock is carried out under a reducing atmosphere, preferably under a hydrogen atmosphere. The hydrogen can be used in pure form or in a mixture. The hydrogen can advantageously come from reforming mono- or poly-oxidized compounds obtained from renewable resources by any reforming method known by one skilled in the art.

Preferably, said method according to the invention is performed at a temperature of between 100° C. and 300° C. and in a preferred manner between 150° C. and 250° C., and at a pressure of between 0.1 MPa and 50 MPa, and in a preferred manner between 0.5 and 30 MPa.

Generally, the method can be performed according to different embodiments. Thus, the method can advantageously be implemented intermittently or continuously, for example in a fixed bed. It is possible to operate in a closed reaction chamber or in a semi-open reactor.

The heterogeneous catalyst(s) is/are introduced into the reaction chamber at a rate of a quantity that corresponds to a ratio by mass of feedstock/heterogeneous catalyst(s) of between 1 and 1,000, preferably between 1 and 500, preferably between 1 and 100, preferably between 1 and 50, and also preferably between 1 and 25.

The heterogeneous catalyst(s) introduced into the reactor can undergo a reducing heat treatment step before the reaction feedstock is introduced. The reducing heat treatment is preferably carried out at a temperature of between 100° C. and 600° C. under a stream of hydrogen or under a hydrogen atmosphere.

The feedstock is introduced in the method at a rate of a quantity that corresponds to a ratio by mass of solvent/feedstock of between 0.1 and 200, preferably between 0.3 and 100, and also preferably between 1 and 50.

If a continuous method is selected, the mass speed per hour (flow rate of mass feedstock/mass of heterogeneous catalyst(s)) is between 0.01 $h^{-1}$ and 5 $h^{-1}$, preferably between 0.02 $h^{-1}$ and 2 $h^{-1}$.

The Products Obtained and the Procedure for Analyzing them

The products of the reaction of the transformation method according to the invention are mono- or poly-oxidized compounds. Said mono- or poly-oxidized compounds are soluble in water, in alcohols and in diols.

Said mono- or poly-oxidized compounds advantageously consist of alcohols, polyols, aldehydes, ketones, carboxylic acids and esters thereof.

Alcohol refers to methanol, ethanol, propanols, butanols, pentanols and hexanols.

Polyols refers to:
Diols such as ethylene glycol, propylene glycol, 1,3-propanediol, 1,2-butanediol, 2,3-butanediol, 1,4-butanediol, pentanediols, hexanediols.
Triols such as glycerol, 1,2,3-butanetriol, 1,2,4-butanetriol, pentanetriols, hexanetriols.
Tetrols such as erythritol, pentanetetrols, hexanetetrols.
Aldehyde refers to, for example, glycolaldehyde, glyceraldehyde.
Ketone refers to, for example, hydroxyacetone.
Carboxylic acid and esters thereof refer to, for example, formic acid, lactic acid, alkyl formates and alkyl lactates.

At the end of the reaction, the reaction medium is analyzed by high pressure liquid chromatography (HPLC) by using refractometry to determine the content of products of conversion of the solution and by gas chromatography (GC).

In the event of a transformation where the solvent is water, the quantity of reaction products that are water-soluble is determined by the TOC (Total Organic Carbon) analysis that consists of the measurement of carbon in solution.

EXAMPLES

In the examples below, the perovskite substrates of the heterogeneous catalysts are commercial.

The substrate of the heterogeneous catalysts that contain cerium oxide is commercial.

In the tables of results, EG represents ethylene glycol and PG represents propylene glycol.

In the tables of results, the yield of monoalcohols represents the sum of the yields obtained of methanol, ethanol, 1-propanol, 2-propanol, 1-butanol, 2-butanol, 1-pentanol, 2-pentanol, 3-pentanol, 1-hexanol, 2-hexanol, 3-hexanol.

Example 1: Preparation of Catalyst C1 Comprising 0.7% by Weight of Pt on a Cerium Oxide Substrate An aqueous solution of hexachloroplatinic acid $H_2PtCl_6.xH_2O$ at 1.9% by weight (25 mL, 0.475 g) is added at ambient temperature to the cerium oxide substrate $CeO_2$ (24 g) that was previously desorbed under vacuum (1 hour, 100° C.). The mixture is stirred for one hour and then evaporated. The solid that is obtained is then placed in the oven at 110° C. to dry for 24 hours. The solid is calcined under a flow rate of dry nitrogen at the temperature of 150° C. for 1 hour, then 250° C. for 1 hour, then 350° C. for 3 hours, and finally 420° C. for 4 hours. It is then reduced under a stream of hydrogen at 500° C. for two hours. The Pt (0.7%)/$CeO_2$ catalyst C1 is thus obtained.

The BET specific surface area of catalyst C1 is 45 $m^2/g$.

Example 2: Preparation of Catalyst C2 Comprising 10% by Weight of Ni on a Perovskite-Type Substrate An aqueous solution of nickel nitrate $Ni(NO_3)_2.6H_2O$ at 10% by weight (25 mL, 2.4 g) is added at ambient temperature to the perovskite-type substrate $BaZrO_3$ (24 g) that was previously desorbed under vacuum (1 hour, 100° C.). The mixture is stirred for one hour and then evaporated. The solid that is obtained is then placed in the oven at 110° C. to dry for 24 hours. The solid is calcined under a stream of dry nitrogen at the temperature of 150° C. for 1 hour, then 250° C. for 1 hour, then 350° C. for 3 hours, and finally 420° C. for 4 hours. It is then reduced under a stream of hydrogen at 500° C. for two hours. The Ni(10%)/$BaZrO_3$ catalyst C2 is thus obtained.

The BET specific surface area of catalyst C2 is 3 $m^2/g$.

Example 3: Preparation of the Ni—MgO Catalyst C3 (Non-Compliant)

An aqueous solution that contains nickel nitrate $Ni(NO_3)_2.6H_2O$ and magnesium nitrate $Mg(NO_3)_2.6H_2O$, with a concentration of metal Ni of 0.3 M and of Mg of 0.7 M, is added at a flow rate of 1 mL/minute to a solution of sodium carbonate $Na_2CO_3$ at 1.2 mol/L at ambient temperature. After one night of stirring, the precipitates are recovered and washed under vacuum to a pH<8 of the filtrate and then dried at 110° C. for 12 hours. They are then calcined at 500° C. for 3 hours under static air and then reduced under hydrogen at 500° C. for 3 hours. Catalyst C3 is thus obtained.

The BET specific surface area of catalyst C3 is 107 $m^2/g$.

Example 4: Transformation of Sorbitol Using Catalyst C1 (Compliant)

Example 4 relates to the conversion of sorbitol in the presence of the heterogeneous catalyst C1 that is described in Example 1 for the production of mono- and poly-oxidized products.

25 mL of water, 0.65 g of sorbitol and 0.275 g of catalyst C1 are introduced under a nitrogen atmosphere into a 100-mL autoclave.

The heterogeneous catalyst is introduced into the reaction chamber at a rate of a quantity that corresponds to a ratio by mass of feedstock/heterogeneous catalyst=2.4.

Sorbitol is introduced into the autoclave at a rate of a quantity that corresponds to a ratio by mass of solvent/sorbitol=38.

The autoclave is heated to 230° C. and a pressure of 2.5 MPa of hydrogen is introduced. After 6 hours of reaction, a sampling of the reaction medium is carried out. It is analyzed by high pressure liquid chromatography (HPLC) by using refractometry for determining the content of products of conversion of the aqueous solution and gas chromatography (GC).

The results that are obtained are referenced in Table 1.

TABLE 1

Transformation of Sorbitol into Mono- and Poly-Oxidized Products

| Conversion (%) | EG Yield (%) | PG Yield (%) | Monoalcohols Yield (%) |
|---|---|---|---|
| 90 | 1.5 | 12 | 4 |

Example 5: Transformation of Xylitol Using Catalyst C1 (Compliant)

Example 5 relates to the conversion of xylitol in the presence of catalyst C1 that is described in Example 1 for the production of mono- and poly-oxidized products.

25 mL of water, 0.65 g of xylitol and 0.275 g of catalyst C1 are introduced under a nitrogen atmosphere into a 100-mL autoclave.

The heterogeneous catalyst is introduced into the reaction chamber at a rate of a quantity that corresponds to a mass ratio of feedstock/heterogeneous catalyst=2.4.

Xylitol is introduced into the autoclave at a rate of a quantity that corresponds to a ratio by mass of solvent/xylitol=38.

The autoclave is heated at 230° C. and a pressure of 2.5 MPa of hydrogen is introduced. After 6 hours of reaction, a sampling of the reaction medium is carried out. It is analyzed by high pressure liquid chromatography (HPLC) by using refractometry to determine the content of products of conversion of the aqueous solution and by gas chromatography (GC).

The results that are obtained are referenced in Table 2.

TABLE 2

Transformation of Xylitol into Mono- and Poly-Oxidized Products

| Conversion (%) | EG Yield (%) | PG Yield (%) | Monoalcohols Yield (%) |
|---|---|---|---|
| 73 | 6 | 7 | 4 |

Example 6: Transformation of Xylitol Using Catalyst C2 (10% by Weight of Ni/BaZrO$_3$) (Compliant)

Example 6 relates to the conversion of xylitol in the presence of catalyst C2 that is described in Example 2 for the production of mono- and poly-oxidized products.

25 mL of water, 0.65 g of xylitol, and 0.275 g of catalyst C2 are introduced under a nitrogen atmosphere into a 100-mL autoclave.

The heterogeneous catalyst is introduced into the reaction chamber at a rate of a quantity that corresponds to a ratio by mass of feedstock/heterogeneous catalyst=2.4.

Xylitol is introduced into the autoclave at a rate of a quantity that corresponds to a ratio by mass of solvent/xylitol=38.

The autoclave is heated at 230° C., and a pressure of 2.5 MPa of hydrogen is introduced. After 6 hours of reaction, a sampling of the reaction medium is carried out. It is analyzed by high pressure liquid chromatography (HPLC) by using refractometry for determining the content of products of conversion of the aqueous solution and by gas chromatography (GC).

The results that are obtained are referenced in Table 3.

TABLE 3

Transformation of Xylitol into Mono- and Poly-Oxidized Products

| Conversion (%) | EG Yield (%) | PG Yield (%) | Monoalcohols Yield (%) |
|---|---|---|---|
| 70 | 1.5 | 1.5 | 2.7 |

Example 7: Transformation of Sorbitol Using Catalyst C2 (Compliant)

Example 7 relates to the conversion of sorbitol in the presence of the heterogeneous catalyst C2 that is described in Example 2 for the production of mono- and poly-oxidized products.

25 mL of water, 0.64 g of sorbitol, and 0.275 g of catalyst C2 are introduced under a nitrogen atmosphere into a 100-mL autoclave.

The heterogeneous catalyst is introduced into the reaction chamber at a rate of a quantity that corresponds to a ratio by mass of feedstock/heterogeneous catalyst=2.3.

Sorbitol is introduced into the autoclave at a rate of a quantity that corresponds to a ratio by mass of solvent/sorbitol=39.

The autoclave is heated at 230° C., and a pressure of 2.5 MPa of hydrogen is introduced. After 6 hours of reaction, a sampling of the reaction medium is carried out. It is analyzed by high pressure liquid chromatography (HPLC) by using refractometry for determining the content of products of conversion of the aqueous solution and by gas chromatography (GC).

The results that are obtained are referenced in Table 4.

TABLE 4

Transformation of Sorbitol into Mono- and Poly-Oxidized Products

| Conversion (%) | EG Yield (%) | PG Yield (%) | Monoalcohols Yield (%) |
|---|---|---|---|
| 95 | 5.5 | 4.5 | 8 |

Example 8: Transformation of Glucose Using Catalyst C1 (Compliant)

Example 8 relates to the conversion of glucose in the presence of the heterogeneous catalyst C1 that is described in Example 1 for the production of mono- and poly-oxidized products.

25 mL of water, 0.64 g of glucose, and 0.275 g of catalyst C1 are introduced under a nitrogen atmosphere into a 100-mL autoclave.

The heterogeneous catalyst is introduced into the reaction chamber at a rate of a quantity that corresponds to a ratio by mass of feedstock/heterogeneous catalyst=2.3.

Glucose is introduced into the autoclave at a rate of a quantity that corresponds to a ratio by mass of solvent/glucose=39.

The autoclave is heated at 230° C., and a pressure of 2.5 MPa of hydrogen is introduced. After 6 hours of reaction, a sampling of the reaction medium is carried out. It is analyzed by high pressure liquid chromatography (HPLC) by using refractometry for determining the content of products of conversion of the aqueous solution and by gas chromatography (GC).

The results that are obtained are referenced in Table 5.

TABLE 5

Transformation of Glucose into Mono- and Poly-Oxidized Products

| Conversion (%) | EG Yield (%) | PG Yield (%) | Monoalcohols Yield (%) |
|---|---|---|---|
| 98 | 4 | 13 | 16 |

Example 9: Transformation of a Mixture of Xylose and Glucose Using Catalyst C2 (10% by Weight of Ni/BaZrO$_3$) (Compliant)

Example 9 relates to the conversion of a mixture of xylose and glucose in the presence of catalyst C2 that is described in Example 2 for the production of mono- and poly-oxidized products.

25 mL of water, 0.32 g of xylose, 0.32 g of glucose, and 0.275 g of catalyst C2 are introduced under a nitrogen atmosphere into a 100-mL autoclave.

The heterogeneous catalyst is introduced into the reaction chamber at a rate of a quantity that corresponds to a ratio by mass of feedstock/heterogeneous catalyst=2.3.

Xylose and glucose are introduced into the autoclave at a rate of a quantity that corresponds to a ratio by mass of solvent/(xylose+glucose)=39.

The autoclave is heated at 230° C., and a pressure of 2.5 MPa of hydrogen is introduced. After 6 hours of reaction, a sampling of the reaction medium is carried out. It is analyzed by high pressure liquid chromatography (HPLC) by using refractometry for determining the content of products of conversion of the aqueous solution and by gas chromatography (GC).

The results that are obtained are referenced in Table 6.

TABLE 6

Transformation of a Mixture of Xylose and Glucose into Mono- and Poly-Oxidized Products

| Conversion (%) | EG Yield (%) | PG Yield (%) | Monoalcohols Yield (%) |
|---|---|---|---|
| 98 | 12 | 12 | 13 |

Example 10: Transformation of a Mixture of Xylitol and Sorbitol Using Catalyst C1 (0.7% by Weight of Pt/CeO$_2$) (Compliant)

Example 10 relates to the conversion of a mixture of xylitol and sorbitol in the presence of catalyst C1 that is described in Example 1 for the production of mono- and poly-oxidized products.

25 mL of water, 0.325 g of xylitol, 0.325 g of sorbitol, and 0.275 g of catalyst C1 are introduced under a nitrogen atmosphere into a 100-mL autoclave.

The heterogeneous catalyst is introduced into the reaction chamber at a rate of a quantity that corresponds to a ratio by mass of feedstock/heterogeneous catalyst=2.4.

Xylitol and sorbitol are introduced into the autoclave at a rate of a quantity that corresponds to a ratio by mass of solvent/(xylitol+sorbitol)=38.

The autoclave is heated at 230° C., and a pressure of 2.5 MPa of hydrogen is introduced. After 6 hours of reaction, a sampling of the reaction medium is carried out. It is analyzed by high pressure liquid chromatography (HPLC) by using refractometry for determining the content of products of conversion of the aqueous solution and by gas chromatography (GC).

The results that are obtained are referenced in Table 7.

TABLE 7

Transformation of a Mixture of Xylitol and Sorbitol into Mono- and Poly-Oxidized Products

| Conversion (%) | EG Yield (%) | PG Yield (%) | Monoalcohols Yield (%) |
|---|---|---|---|
| 96 | 10 | 14 | 9 |

Example 11: Transformation of Sorbitol Using the Ni—MgO Catalyst C3 (Non-Compliant)

Example 11 relates to the conversion of sorbitol in the presence of the heterogeneous catalyst C3 that is described in Example 3 for the production of mono- and poly-oxidized products.

25 mL of water, 0.64 g of sorbitol, and 0.275 g of catalyst C3 are introduced under a nitrogen atmosphere into a 100-mL autoclave.

The heterogeneous catalyst is introduced into the reaction chamber at a rate of a quantity that corresponds to a ratio by mass of feedstock/heterogeneous catalyst=2.3.

Sorbitol is introduced into the autoclave at a rate of a quantity that corresponds to a ratio by mass of solvent/sorbitol=38.

The autoclave is heated at 230° C., and a pressure of 2.5 MPa of hydrogen is introduced. After 6 hours of reaction, a sampling of the reaction medium is carried out. It is analyzed by high pressure liquid chromatography (HPLC) by using refractometry for determining the content of products of conversion of the aqueous solution and by gas chromatography (GC).

The results that are obtained are referenced in Table 8.

TABLE 8

Transformation of Sorbitol into Mono- and Poly-Oxidized Products

| Conversion (%) | EG Yield (%) | PG Yield (%) | Monoalcohols Yield (%) |
|---|---|---|---|
| 68 | 18 | 22 | 6 |

Example 12: Analysis of Catalysts C1, C2 and C3 after Reaction

The BET specific surface area of the fresh heterogeneous catalyst C1 is 45 m$^2$/g; the BET specific surface area of catalyst C1 after reaction is 40 m$^2$/g; it is therefore reduced by 12% in relation to the fresh heterogeneous catalyst. The structure of the spent heterogeneous catalyst C1 that is analyzed by XRD is identical to that of the fresh heterogeneous catalyst C1. Compositional analysis shows that less than 20% of the elements have been lixiviated.

The BET specific surface area of the fresh heterogeneous catalyst C2 is 3 m$^2$/g; the BET specific surface area of catalyst C2 after reaction is 3 m$^2$/g; it is therefore identical in relation to the fresh heterogeneous catalyst. The structure of the spent heterogeneous catalyst C2 that is analyzed by XRD is identical to that of the fresh heterogeneous catalyst C2. Compositional analysis shows that less than 20% of the elements have been lixiviated.

The BET specific surface area of the fresh heterogeneous catalyst C3 is 107 m$^2$/g; the BET specific surface area of catalyst C3 after reaction is 54 m$^2$/g; it is therefore reduced by 50% in relation to the fresh heterogeneous catalyst. The structure of the spent heterogeneous catalyst C3 that is analyzed by XRD shows the formation of new MgO, MgNiO$_2$ and MgCO$_3$ phases corresponding to a degradation of the catalyst. Compositional analysis shows that 28% of the elements have been lixiviated.

The heterogeneous catalysts C1 and C2 according to the invention are therefore hydrothermally stable according to the definition of the invention.

The heterogeneous catalyst C3 is therefore not hydrothermally stable according to the definition of the invention.

Thus, the heterogeneous catalysts C1 and C2 can be engaged again in a method for transformation of sugars and sugar alcohols into mono- and poly-oxidized compounds whereas catalyst C3 cannot be reused.

The invention claimed is:

1. A method for transforming a feedstock that is a sugar or sugar alcohol, alone or in a mixture, into mono- or poly-oxidized compounds, comprising contacting said feedstock with at least one heterogeneous catalyst, in the same reaction chamber, in the presence of at least one solvent, with said solvent being water, an alcohol, a diol, or another solvent, by itself or in a mixture, under a reducing atmosphere, and at a temperature of between 100° C. and 300° C., and at a pressure of between 0.1 MPa and 50 MPa, and in which said heterogeneous catalyst(s) comprise(s) at least one metal that is a metal of groups 8 to 11 of the periodic table and a substrate that is a perovskite of formula ABO$_3$ in which A is Mg, Ca, Sr or Ba, and B is Fe, Mn, Ti or Zr, or an oxide of lanthanum, neodymium, yttrium, or cerium, by themselves or in a mixture, with said oxide able to be doped by at least one alkali metal, alkaline-earth, or rare earth, by themselves or in a mixture, with said method being performed in the absence of additional catalyst.

2. The method according to claim 1, in which said method is performed in the absence of additional basic catalyst that is an oxide, hydroxide or alcoholate of alkali or alkaline-earth metal, which may or may not be hydrated, having as a formula M$_m$X$_n$.n' H$_2$O in which the metal M is a metal of group 1 or 2 of the periodic table, m is a whole number of between 1 and 2, n is a whole number of between 1 and 2, and n' is a number of between 0 and 20, and X is oxygen, a hydroxyl group or an alcoholate groups of formula OR with R an alkyl group.

3. The method according to claim 1, in which the feedstock is a sugar that is an oligosaccharide or monosaccharide, by themselves or in a mixture.

4. The method according to claim 3, in which the oligosaccharide is saccharose, lactose, maltose, isomaltose, inulobiose, melibiose, gentiobiose, trehalose, cellobiose, cellotriose, cellotetraose, or an oligosaccharide that is obtained from hydrolysis of starch, inulin, cellulose or hemicellulose, by themselves or in a mixture.

5. The method according to claim 3, in which the monosaccharide is dihydroxyacetone, erythrose, xylose, arabinose, glucose, mannose, or fructose, by themselves or in a mixture.

6. The method according to claim 1, in which the feedstock is a sugar alcohol that is lactitol, maltitol, isomaltitol, inulobitol, melibitol, gentiobitol, cellobitol, cellotritol, cellotetritol, glycerol, erythritol, xylitol, arabinitol, sorbitol, or mannitol, by themselves or in a mixture.

7. The method according to claim 1, in which the metals of groups 8 to 11 of the periodic table of said heterogeneous catalyst(s) are Fe, Ru, Os, Co, Rh, Ir, Ni, Pd, Pt, Cu, Ag or Au, by themselves or in a mixture.

8. The method according to claim 1, in which the perovskite of formula ABO$_3$ is BaTiO$_3$, SrTiO$_3$, BaZrO$_3$, CaZrO$_3$, SrZrO$_3$, or CaMnO$_3$.

9. The method according to claim 1, in which said oxides are doped by at least one doping element, that is Li, Na, K, Rb, Cs, Be, Mg, Ca, Sr, Ba, La, Ce, Sm, Gd, Y, or Pr, by themselves or in a mixture.

10. The method according to claim 9, in which the doping element has a content of between 0.1% and 30% by weight in relation to the total mass of said substrate.

11. The method according to claim 1, in which the solvent is water, ethylene glycol, propylene glycol, methanol, ethanol, or a propanol, by themselves or in a mixture.

12. The method according to claim 11, in which solvents comprises a mixture having a content by mass of water that is greater than 5% by weight in relation to the total mass of said mixture.

13. The method according to claim 1, in which the temperature is between 150° C. and 250° C. and the pressure is between 0.5 MPa and 30 MPa.

14. The method according to claim 1, in which said heterogeneous catalyst is introduced into the reaction chamber with a ratio by mass of feedstock/heterogeneous catalyst of between 1 and 500.

15. The method according to claim 11, in which the solvent comprises a mixture having a content by mass of water that is greater than 30% by weight in relation to the total mass of said mixture.

16. The method according to claim 11, in which the solvent comprises a mixture having a content by mass of water that is greater than 50% by weight in relation to the total mass of said mixture.

* * * * *